US00PP31395P2

(12) United States Plant Patent
Hansen

(10) Patent No.: US PP31,395 P2
(45) Date of Patent: Jan. 21, 2020

(54) ***HEUCHERA* PLANT NAMED 'MAHOGANY MONSTER'**

(50) Latin Name: ***Heuchera* hybrid**
Varietal Denomination: Mahogany Monster

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,004

(22) Filed: Sep. 10, 2018

(51) Int. Cl.
*A01H 5/12* (2018.01)

(52) U.S. Cl.
USPC ..... Plt./440

(58) Field of Classification Search
USPC ..... Plt./440

CPC ... A01H 5/02; A01H 5/12; A01H 5/00; A01H 5/025; A01H 6/80
See application file for complete search history.

(56) References Cited

PUBLICATIONS

Christian County Master Gardener Association News 2017, retrieved on Jun. 17, 2019, retrieved from the Internet at https://christian.ca.uky.edu/files/january_mg_news_0.pdf, 4 pp. (Year: 2017).*

* cited by examiner

*Primary Examiner* — June Hwu

(57) ABSTRACT

The new and distinct hybrid of *Heuchera* plant named 'Mahogany Monster' with very large foliage having rounded apices and lobes, leaf blades begin the season deep glowing red and develop to dark mahogany without silver overlay surrounding the veins. Numerous, densely-branched, stiff, erect, very large, wine-colored panicles display bright pink calyces with near white petals for about five weeks beginning late spring and repeating through the summer. The new plant is vigorous and produces large broadly-mounded clumps.

2 Drawing Sheets

Botanical denomination: *Heuchera* hybrid.
Variety denomination: 'Mahogany Monster'.

BACKGROUND OF THE INVENTION

The present invention relates to a new and distinct cultivar of Coral Bells in the Saxifragaceae family and given the cultivar name of 'Mahogany Monster'. *Heuchera* 'Mahogany Monster' was hybridized by the inventor on Mar. 31, 2015 at a wholesale perennial nursery in Zeeland, Mich., USA. The seed or female parent was the proprietary unreleased hybrid known as 13-764-2 and the pollen or male parent was the proprietary unreleased hybrid known as 13-700-1.

*Heuchera* 'Mahogany Monster' was first selected in the fall of 2016 and assigned the breeder code 15-225-4 through the final evaluation process in the fall of 2017 when it was selected from among many other seedlings from the same cross and hundreds of other crosses. *Heuchera* 'Mahogany Monster' has been asexually propagated by division at the same nursery in Zeeland, Mich. in 2016 and by sterile, shoot-tip, tissue culture propagation, and the resultant plants have remained stable and continued to exhibit the same characteristics as the original plant for multiple generations.

No plants of *Heuchera* 'Mahogany Monster' have been sold, in this country or anywhere in the world, prior to the filing of this application, nor has any disclosure of the new plant been made prior to the filing of this application with the exception of that which was disclosed within one year of the filing of this application, and was either derived directly or indirectly from the inventor.

BRIEF SUMMARY OF THE INVENTION

The nearest comparison varieties include: 'Mahogany' U.S. Plant Pat. No. 19,072, 'Fire Chief' U.S. Plant Pat. No. 21,880, 'Cajun Fire' U.S. Plant Pat. No. 24,150 and 'Cherry Truffles' U.S. Plant patent application Ser. No. 16/350,002. 'Mahogany' has smaller leaf blades with brighter and lighter reddish spring foliage color, and the flowers are small with the effect creamy-white rather than pink. 'Fire Chief' has smaller leaf blades that are brighter reddish and less darker greyed-purple and the scapes are much smaller in diameter and shorter with fewer flowers per peduncle. 'Cajun Fire' has smaller leaf blades with brighter reddish foliage in the spring and darker area around the veins, while also having white to creamy white flowers. Compared with co-pending 'Cherry Truffles' the new plant has larger and darker mahogany foliage, and the habit of the new plant is a broader mound. The female was not maintained and no photographs of it were saved, so no comparison is possible. The male parent is smaller in leaf and habit and more reddish in foliage color with shorter flower scapes.

*Heuchera* 'Mahogany Monster' differs from its parents as well as all other coral bells known to the applicant in the following combined traits:

1. The very large foliage has rounded apices and lobes.
2. Huge leaf blades begin season deep glowing red and develop into dark mahogany without silver overlay surrounding the veins.
3. Leaf blade are shallowly dissected with apices rounded with tiny sharp tips.

4. Flowers provide a bright pink effect from calyces with near white petals.
5. Numerous, stiff, erect, very large in both diameter and height, densely-branched panicles of wine-colored stems display flowers above foliage beginning late spring with repeating panicles through the summer.
6. The new plant is vigorous and produces large broadly-mounded clumps.

BRIEF DESCRIPTION OF THE DRAWINGS

The photographs of the new plant demonstrate the overall appearance of the plant including the unique traits. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
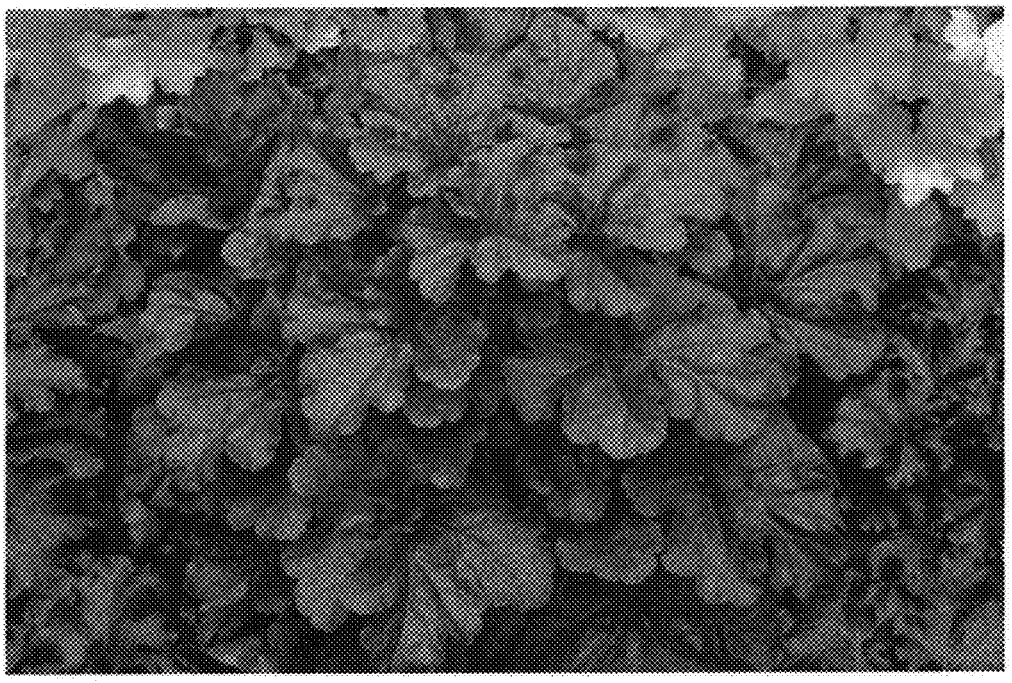
FIG. 1 shows a one-year-old plant with spring foliage before flowering.
Figure 2:
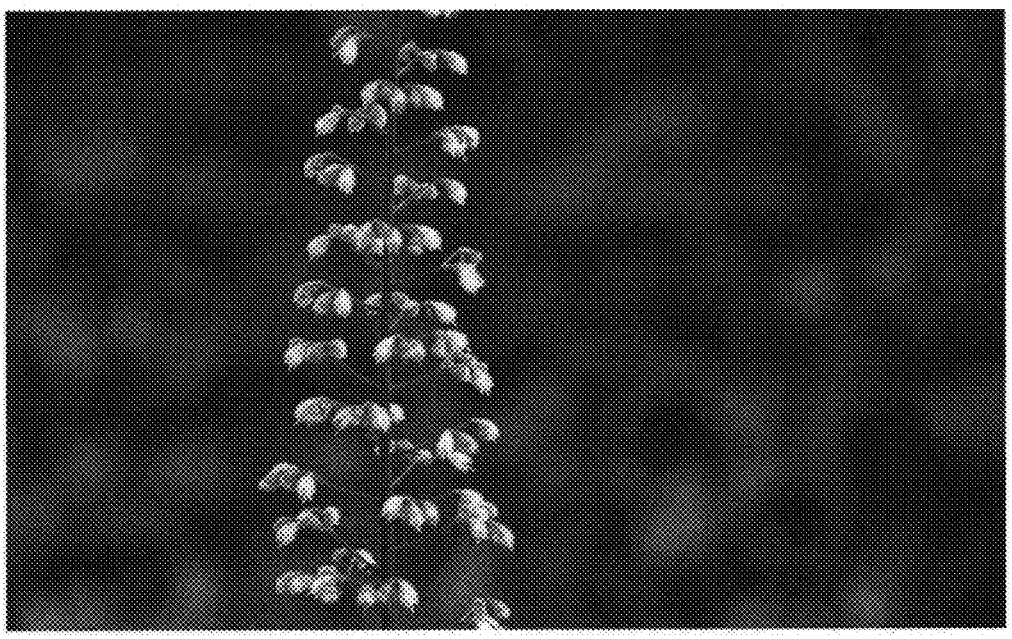
FIG. 2 shows a close-up of a flower panicle with buds and flowers from a one-year-old plant.
Figure 3:
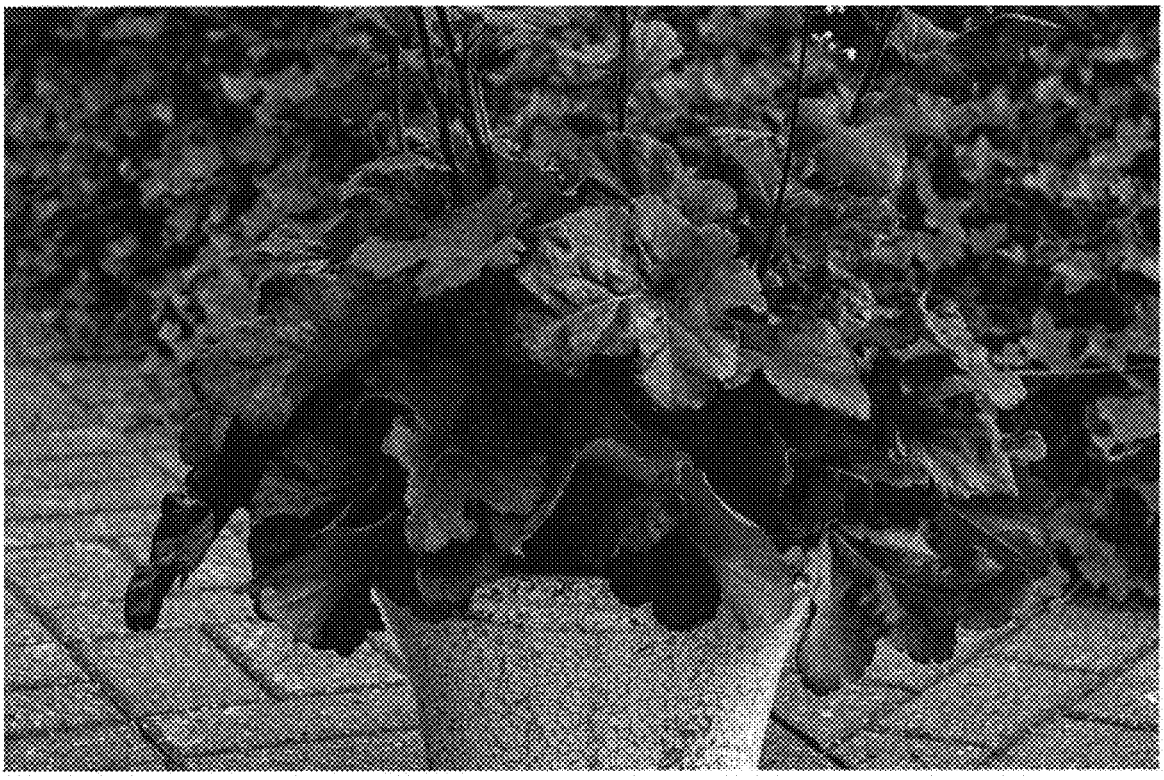
FIG. 3 shows a two-year-old greenhouse grown plant in later stage of flowering.

The following description is based on a two-year-old plant growing in a partially shaded greenhouse in Zeeland, Mich., USA. The new plant has not been grown under all possible environments and may phenotypically appear different under different conditions such as light, temperatures, fertilizer, and water, without any difference in genotype. The color descriptions used are from The 2015 edition of The Royal Horticultural Society Colour Chart except where common dictionary terms are used.

Parentage: Female or seed parent was the unreleased proprietary hybrid 13-764-2 with 'Cajun Fire' U.S. Plant Pat. No. 24,150, 'Mocha' U.S. Plant Pat. No. 18,386 along with a proprietary selection of *Heuchera hallii* in the ancestry, the male or pollen parent was the proprietary unreleased hybrid known only by the breeder code 13-700-1 (not patented) with 'Cherry Cola' U.S. Plant Pat. No. 22,967, 'Hercules' (not patented), 'Dark Mystery' (not patented) and 'Fire Chief' U.S. Plant Pat. No. 21,880 in the ancestry;

Plant habit: Hardy herbaceous perennial with basal rosette of foliage; broadly mounded foliage about 30.0 cm tall and 74.0 cm in diameter with stapes to about 71.0 cm long; with 10 stems per plant to about 3.5 cm long and 2.0 cm diameter at base, with about 10 to 14 leaves per stem; about 34 panicles per plant;

Roots: Fibrous, finely branched;

Growth rate: Rapid, rooting from cutting in two weeks and finishing in three-liter container in about two and a half months;

Foliage: Cordate to nearly ovate; minutely puberulent adaxial and abaxial; palmately shallowly lobed with five main lobes, shallowly to moderately dissected less than one-fourth of the way to petiole; apex and lobe apices rounded; base cordate with basal lobes nearly overlapping to overlapping about 3.5 cm; margins crenate to mucronulate, micro-ciliolate; lustrous adaxial and abaxial with medium glossiness; slightly ruffled; held upright near plant center to arching for outer leaves; margin slightly sinuate; surface highly rugose when young and becoming slightly rugose when mature;

Leaf blade size: To about 19.0 cm wide and 19.5 cm long, average about 15.5 cm wide and 16.0 cm long;

Leaf color: Spring and young emerging leaves adaxial between RHS 187C and RHS 187B with no silver and dark green marbling surrounding the veins, spring young emerging leaves abaxial nearest RHS 59A; mature mid-season leaves adaxial nearest RHS N186C without lighter marbling or darker colors surrounding the veins, abaxial mature mid-season leaves nearest RHS 187B; fall and winter color adaxial variable, nearest RHS NN137A, N187A and RHS 187A without lighter marbling or darker colors surrounding the veins, fall and winter color abaxial nearest RHS 187B;

Leaf quantity: Dense, about 110 per plant;

Veins: Palmate, hirsutulous abaxial and puberulent adaxial; costate abaxial, slightly impressed adaxial;

Vein color: Emerging or early spring adaxial basal midrib nearest RHS 186A and secondary and distal veins nearest RHS 187C with emerging spring abaxial nearest RHS N186D; mid-season and flowering time adaxial nearest RHS 183D, mid-season and flowering time abaxial nearest RHS 187B; fall adaxial variable, nearest a blend of RHS 189A and RHS 187B toward petiole and distally becoming nearest RHS 187A, fall abaxial midrib base nearest 182B with distal and secondary veins becoming nearest RHS 187B;

Petiole: Terete, base amplexicaul; with pubescent hairs to about 2.0 mm long; to about 30.0 cm long and 7.0 mm wide before average about 21.0 cm long and about 4.5 mm diameter above stipule and 14.0 mm at base including stipule;

Petiole color: Emerging leaf nearest RHS N186D; flowering season mature leaf nearest RHS 187B; autumn season nearest RHS 187B with slight undertone of nearest RHS 189B;

Stipule: Flared at base of petiole; glaucous adaxial and abaxial with ciliolate margin; to about 2.0 cm long and about 1.4 cm wide at base; with two distal lateral projections of about 3.0 mm long in distal portion;

Stipule color: Young expanding leaf adaxial and abaxial nearest RHS N186D; mature leaf adaxial center nearest 70A surrounded by RHS 187B, abaxial nearest RHS N186C;

Peduncle: Panicle; terete; stiff; pubescent; upright; densely branched; to about 74.0 cm long and 6.0 mm diameter at base, average about 68.0 cm tall and 5.0 mm diameter; about ten per plant with up to about 275 flowers per panicle, average about 230; tightly-branched panicle with up to 35 branches up to about 5.5 cm long and 0.5 mm diameter decreasing distally, average 30 branches per panicle; lower branches about 45 degree above horizontal, becoming nearly horizontally in distal 6.0 cm of panicle; flower density heavy;

Flowering longevity: Panicle effective for about four to five weeks; individual flowers about 5 days; self-cleaning;

Peduncle color: Nearest RHS 186A at beginning anthesis, becoming nearest RHS 187A distally and with latter flowers; with about 11 cauline leaves below flower, spaced about 1.2 cm apart;

Cauline leaves: Palmate; incised margin; puberulent abaxial and adaxial; petiolate; blade about 8.0 mm across and 8.0 mm long, petiole about 8.0 mm long, with two stipules at base about 7.0 mm long; cauline leaves, petiole and stipule decreasing distally to become bracts subtending peduncle branches; stipules lanceolate with acute apex, truncate base and ciliate margin;

Cauline leaf color: Adaxial blade nearest RHS 183A, abaxial nearest RHS 187B; petiole nearest RHS 187B and stipule adaxial and abaxial nearest RHS N186D;

Pedicel: Terete, pubescent; to about 4.0 mm long and 0.5 mm diameter, average about 2.0 mm long and 0.5 mm diameter; attitude outwardly to slightly drooping;

Pedicel color: Nearest RHS 187C lightening with age;

Buds one day prior to opening: Ellipsoid; rounded apex and attenuate base; glandular; about 5.0 mm long and 3.0 mm diameter;

Bud color one day prior to opening: Nearest RHS 64C in basal one-half and between RHS 64B and RHS 64C in distal one-half;

Flower: Perfect; campanulate; actinomorphic; about 8.0 mm long to tip of exserted style and 4.0 mm in diameter at corolla face;

Flower attitude: Slightly drooping;

Calyx: Five, apex rounded, base fused in proximal 4.0 mm to form hypanthium; puberulent to glandular abaxial, glabrous adaxial; about 5.5 mm long and 4.0 mm wide at apex;

Sepals: Five; lanceolate; acute apex, fused in basal 4.0 mm; to about 5.5 mm long and 2.0 mm wide at fusion;

Sepal color: Abaxial apex nearest RHS 64A and between RHS 64B and RHS 64C proximally, adaxial apex nearest RHS 64A and proximally nearest RHS 70D;

Petals: Five; oblanceolate to spatulate; subacute apex and attenuate base; entire; glabrous abaxial and adaxial; about 3.0 mm long and 1.0 mm wide in middle;

Petal color: Abaxial and adaxial nearest RHS NN155D with very faint blush of light pink;

Androecium: Five adnate to adaxial sepal about 1.0 mm above base;

*Filaments.*—Five, thin, glabrous; about 2.5 mm long and less than 0.3 mm diameter; color nearest RHS 155B.

*Anthers.*—Ellipsoidal, distinct, basifixed, longitudinal; about 0.7 mm long and about 0.5 mm across; color nearest RHS 14C.

*Pollen.*—Abundant; color nearest RHS 17B.

Gynoecium: One, two-beaked; half-inferior; bifid style with pistil split at ovary; about 7.0 mm long;

*Style.*—Bifid; split apart at apex of ovary; exserted; about 5.0 mm long and about 0.5 mm diameter; color nearest RHS N155B.

*Stigma.*—Acute apex, about 0.1 mm diameter; color nearest RHS N155B.

*Ovary.*—Half-inferior, about 2.0 mm long and 2.0 mm diameter; ellipsoidal to globose, base rounded; color nearest RHS 157A.

Fruit: Small two-beaked capsule; about 2.5 mm long and 2.5 mm across; drying to blend between RHS 199A and RHS N199C;

Seeds: Abundant; slightly flattened ellipsoid; about 0.7 mm long, 0.5 mm across and about 0.3 mm thick; color nearest RHS 202A;

Disease and pest tolerance: The new plant grows best with ample moisture and drainage in either part sun or full shade. Cold hardy from USDA zones 4 to 9. Other resistance and tolerance outside of that normal for *Heuchera* is not known.

It is claimed:

1. The new and distinct coral bells plant named *Heuchera* 'Mahogany Monster' as herein described and illustrated.

* * * * *